United States Patent
Shayan

(10) Patent No.: US 6,990,978 B2
(45) Date of Patent: Jan. 31, 2006

(54) METHOD AND SYSTEM FOR VAPORIZATION OF A SUBSTANCE

(76) Inventor: Shaahin Sean Shayan, Advanced Inhalation Revolutions Inc., 12611 W. Washington Blvd., Los Angeles, CA (US) 90066

( * ) Notice: Subject to any disclaimer, the term of this patent is extended or adjusted under 35 U.S.C. 154(b) by 0 days.

(21) Appl. No.: 10/846,824

(22) Filed: May 14, 2004

(65) Prior Publication Data

US 2004/0211418 A1  Oct. 28, 2004

Related U.S. Application Data

(63) Continuation of application No. 10/071,794, filed on Feb. 9, 2002, now Pat. No. 6,772,756.

(51) Int. Cl.
*A61M 16/00* (2006.01)

(52) U.S. Cl. .................. 128/203.27; 128/204.17; 128/202.21; 239/136

(58) Field of Classification Search .......... 128/203.26, 128/203.27, 203.17, 202.21, 204.17, 203.12; 131/194; 261/DIG. 65; 239/136; 392/386, 392/390, 397; 96/361, 362, 363
See application file for complete search history.

(56) References Cited

U.S. PATENT DOCUMENTS

| | | | | |
|---|---|---|---|---|
| 3,695,267 A | * | 10/1972 | Hirtz et al. | 128/203.17 |
| 3,872,280 A | * | 3/1975 | Van Dalen | 392/390 |
| 3,949,743 A | * | 4/1976 | Shanbrom | 128/200.14 |
| 4,291,838 A | * | 9/1981 | Williams | 239/138 |
| 4,399,349 A | * | 8/1983 | Deming et al. | 392/403 |
| 4,708,831 A | * | 11/1987 | Elsworth et al. | 261/130 |
| 4,947,875 A | * | 8/1990 | Brooks et al. | 131/330 |
| 5,086,766 A | * | 2/1992 | Beacham | 128/203.27 |
| 5,195,514 A | * | 3/1993 | Liu et al. | 128/203.17 |
| 5,336,156 A | * | 8/1994 | Miller et al. | 600/22 |
| 5,363,842 A | * | 11/1994 | Mishelevich et al. | 128/200.14 |
| 5,558,084 A | * | 9/1996 | Daniell et al. | 128/203.17 |
| 5,649,554 A | * | 7/1997 | Sprinkel et al. | 131/329 |
| 6,050,260 A | * | 4/2000 | Daniell et al. | 128/204.22 |
| 6,202,642 B1 | * | 3/2001 | McKinnon et al. | 128/200.23 |
| 6,481,437 B1 | * | 11/2002 | Pate | 128/203.26 |
| 6,513,524 B1 | * | 2/2003 | Storz | 128/203.26 |
| 6,772,756 B2 | * | 8/2004 | Shayan | 128/203.26 |

* cited by examiner

*Primary Examiner*—Mital Patel
(74) *Attorney, Agent, or Firm*—Jeffrey Fuer; Jennifer Meredith

(57) ABSTRACT

The present invention provides an apparatus for the vaporization of materials that releases active constituents for inhalation without the creation of harmful byproducts such as carcinogens associated with combustion and inhalation of substances.

7 Claims, 4 Drawing Sheets

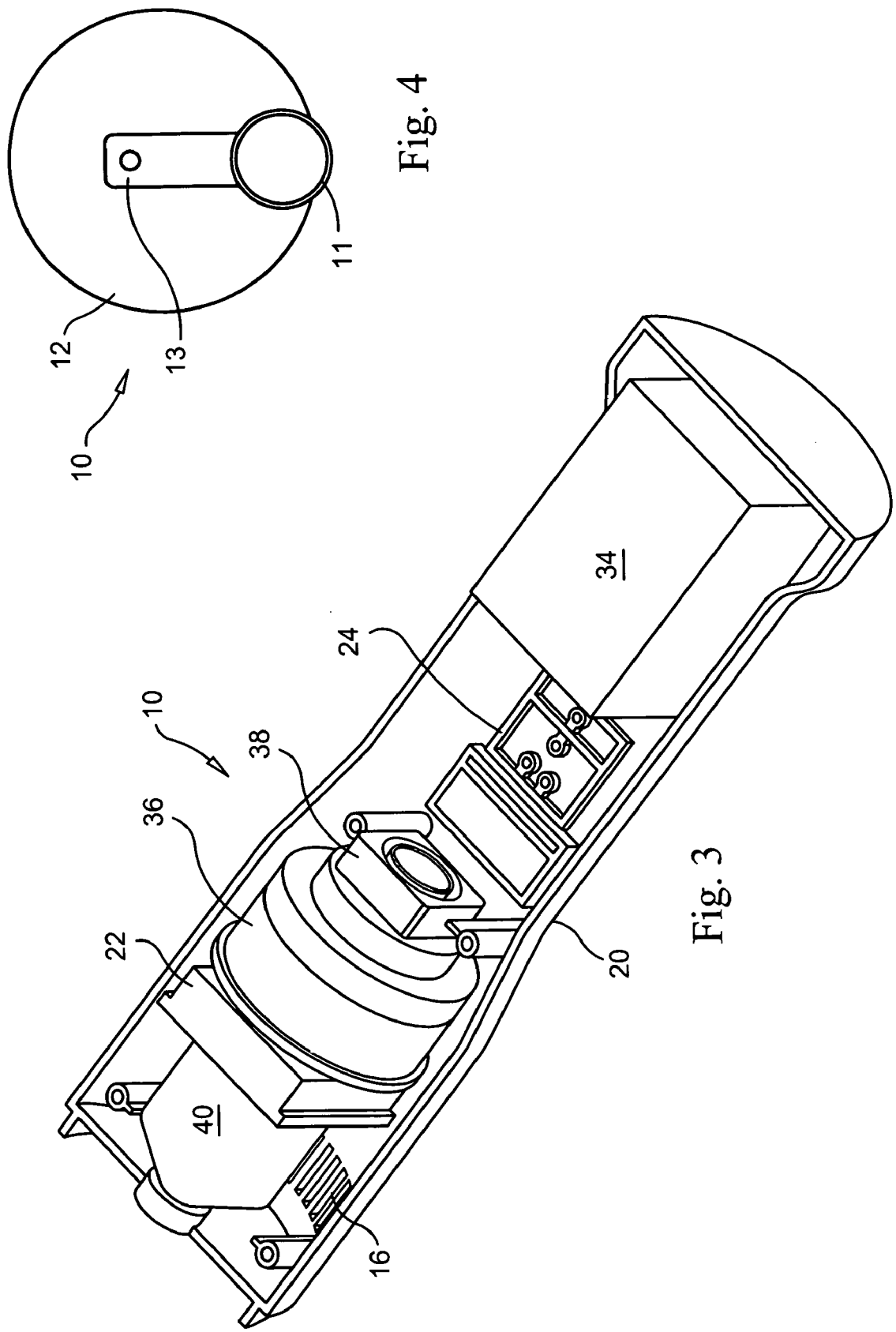

Step 198: heating a substance using a heating means.

↓

Step 199: inputting information manually into an information input/output means, and adjusting the temperature within said apparatus for a specified period of time according to information obtained from the information input/output means.

↓

Step 200: providing a variable heat by the time and temperature control means according to the specific substance being volatized in the apparatus.

↓

Step 202: delivering air using a fan means to create an air stream.

↓

Step 204: combining heat from the heating means and the air stream to provide a convection air stream.

↓

Step 206: delivering the convection air stream according to information provided by the information retrieval and delivery means.

↓

Step 208: delivering the convection air stream according to information provided by the temperature control means.

↓

Step 210: directing the convection air stream over a source material holder, wherein the source material holder may include a cavity for holding a substance.

↓

Step 212: creating a substance vapor air stream.

↓

Step 214: releasing volatile elements from the opening into the ambient air.

↓

Step 216: receiving the substance vapor air stream by the venture tube receptacle, wherein the venture tube receptacle may have at least one opening in communication with the source material holder.

Figure 5

METHOD AND SYSTEM FOR VAPORIZATION OF A SUBSTANCE

This is a continuation of U.S. patent application Ser. No. 10/071,794 now U.S. Pat. No. 6,772,756, which was filed on Feb. 9, 2002.

BACKGROUND OF THE INVENTION

The present invention generally relates to devices for the inhalation of volatile components of a substance, or more particularly to a sophisticated apparatus for the vaporization of materials that release active constituents for inhalation without the creation of harmful byproducts associated with combustion of materials, which is easy to use and provides accurate temperature control and air flow.

Well known within the art is the use of combustion of substances to enable inhalation of volatile materials contained therein. However, recently the hazards associated with such behavior has become well known and of great concern. This process is known as "smoking" and generally involves oxidation, hydrogenation, cracking, distillation and sublimation. Oxidation, hydrogenation, and cracking result in the formation of chemical compounds not present in the original source material and it is these products not present in the original source material that are generally recognized as the most hazardous aspect of smoking. As such it is desirable to heat a substance such that distillation and sublimation occur without combustion. By eliminating combustion as a heat source, the health risks are minimized while enabling the beneficial properties present in the volatile compounds to be utilized.

Plant matter such as tobacco or other herbal medicines, when smoked are also not properly utilized to maximum efficiency. As much as 95% of the active material can be wasted in order to absorb 5% or less of the same. Also, much of the active ingredients and helpful medicines are destroyed by combustion. Various attempts have been tried to overcome the problems associated with smoking.

U.S. Pat. No. 5,249,586 issued to Morgan discloses an article in which a replaceable tobacco flavor medium is electrically heated by a set of permanent reusable heaters to evolve inhalable flavors or other components in vapor or aerosol form. Each heater heats only a portion of the available tobacco flavor medium so that a plurality of individual puffs of tobacco flavor substance can be delivered sequentially to the smoker. The tobacco flavor medium preferably contains tobacco materials.

U.S. Pat. No. 5,33,574 issued to Ingebrethsen discloses an aerosol delivery article which provides delivery of aerosol particles of relatively small size without the necessity of exposing the material which is aerosolized to a significant degree of heat or high temperatures. An aerosol forming material is a multi-component material comprising an active ingredient and another ingredient having a relatively low vaporization temperature, and preferably that aerosol forming material is in the form of an emulsion. The aerosol forming material is nebulized so as to provide first stage multi-component aerosol particles of fairly large size. The first stage aerosol particles then are subjected to heat so as to vaporize the other ingredient of that aerosol and cause further dispersion of that first stage aerosol. As such, a second stage aerosol composed of fine particles of active ingredient is provided. The heat used to cause the further dispersion of the first stage aerosol is less than that sufficient to cause vaporization, thermal decomposition or undesirable chemical alteration of the active ingredient.

U.S. Pat. No. 5,144,962 issued to Counts discloses a Flavor Delivery Article Method and Apparatus. The Counts Patent electrically heats a material in order to release the flavor. While the Counts patent represented an advancement within the art, the Counts Patent utilizes direct heat between the heating element and the medium to effect heat transfer by conduction. This method is flawed in that it does not provide for the optimum temperature according to the material. Also, the material is embedded in the apparatus. A more sophisticated apparatus that allows for the efficient release of desirable elements of a substance is needed.

When tobacco is smoked, many toxic & carcinogenic substances are produced in the process of attempting to ignite and absorb the active component—nicotine. However, it may be desirable to have an apparatus which does not ignite the tobacco, but rather allows for the delivery of nicotine into the blood stream without the tar and other carcinogenic compounds associated with smoking. Such an apparatus would be a revolutionary breakthrough for those trying to quit smoking. Further, given the hazards associated with secondary smoke, a smokeless device is needed to protect non-smokers.

Also, a device is needed which may be used to deliver drugs such as morphine and other opiates that are currently being delivered intravenously. This may also solve many of the problems associated with heroin addicts, such as needle sharing which can lead to dangerous exposure to various diseases. A device is needed which would allow for the delivery of such drugs safely. Currently, devices such as nebulizers may be used to accomplish this. Such devices are flawed, though, in that they require special mixtures of the drugs that must be made into a fog using ultrasound. The present invention does not require the drugs to be specially formulated, but rather allows for an apparatus which may adjust the delivery mode according to the substance being used.

This may also be desirable to health care professionals who do not want to risk exposure to diseases by way of administering needles to patients who may have unknown diseases. Any place where a clean, easy and efficient means of delivering the active elements of a substance would benefit from the present invention.

Accordingly, there is a need for a clean and easy to use device that allows for the release of the essential active elements of a substance through vaporization using just enough heat and air to release them without burning the substance and without creating the toxic byproducts of combustion and denaturing of the initial source material while effectively and optimally delivering a multitude of active elements of different substances.

SUMMARY OF THE INVENTION

In one aspect of the present invention, an apparatus for releasing volatile components of a substance is disclosed. The apparatus comprises in combination a power means, a heating means, a fan means sufficient to create an air flow, a temperature sensing means, a time and temperature control means, a source material holder which is insertable and removable for holding the substance, a receptacle for receiving a vapor that results from the release of volatile components created by heated air directed from the heating means over the substance and releasing volatile elements, and an opening for allowing release of the vapor. The receptacle for receiving the vapor may be a venturi tube. There may also be a window means for viewing the vapor, which may contain a light inside. The temperature sensing means may be a thermocouple or resistance temperature detector (RTD). The heating means may be a Ceramic UF Heater. The airflow may be between 0 and 10 Liters/min. The apparatus may release volatile elements into the ambient air. Also, the time and temperature control means may produce a variable heat according to the specific substance being volatized in said apparatus.

According to another embodiment, a system and apparatus is disclosed that allows for the inhalation of the active components of a substance comprising a housing configured and sized to fit in the user's hand during use, a power means that supplies power to a heating means, information retrieval and delivery means, time and temperature control means, information input/output means, display means, fan means and cooling means, wherein the fan means delivers air to create an air stream which combines with heat from the heating means to provide a convection air stream, wherein the fan delivers air according to information provided by the information retrieval and delivery means and/or the time and temperature control means. An air stream is directed over a source material holder which includes a cavity for holding a substance, creating a substance vapor air stream and a receptacle having at least one opening in communication with the source material holder receives the substance vapor air stream. The heater is preferably a Ceramic UF Heater. The apparatus may also release the volatile elements from the opening into the ambient air. Time and temperature control means produces a variable heat according to the specific substance being volatized in the apparatus. There may be a light in the window. Also, as discussed in previous embodiments, the information input/output means may be in electrical communication with the power means and allow for adjustment of the temperature, time and airflow. Information may also be manually entered into said information input/output means which in turn electrically communicates with said power means, heating means and fan means to adjust the temperature within said apparatus for a specified time. The information retrieval and delivery means may be a disk contained within said apparatus which automatically senses the nature of the material. Once the disk senses the nature of the material, it delivers a set of instructions to the apparatus such as to provide an optimal release of volatile elements of the substance. A mesh materials holder contained within said source material holder may be used in order to prevent the inhalation of extraneous particles and to contain the substance. The mesh materials holder may also have a substance embedded in it. According to another embodiment, a pre-formed substance with holes formed to be contained within the source material holder.

According to a preferred embodiment a method of releasing volatile elements of a substance is disclosed comprising the steps of heating a substance using a heating means, delivering air using a fan means to create an air stream, combining heat from the heating means and the air stream to provide a convection air stream, directing the convection air stream over a source material holder, and directing the convection air stream over a source material holder creating a substance vapor air stream.

These and other features, aspects and advantages of the present invention will become better understood with reference to the following drawings, description and claims.

BRIEF DESCRIPTION OF THE DRAWINGS

FIG. 3 is an interior cutaway view of the present invention according to a preferred embodiment;

FIG. 4 is a top view of the present invention according to a preferred embodiment; and FIG. 5 is a flow chart depicting a method of releasing volatile elements of a substance according to a preferred embodiment of the present invention.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides an apparatus for the vaporization of materials that release active constituents for inhalation without the creation of harmful byproducts associated with combustion of materials.

Figure 1:
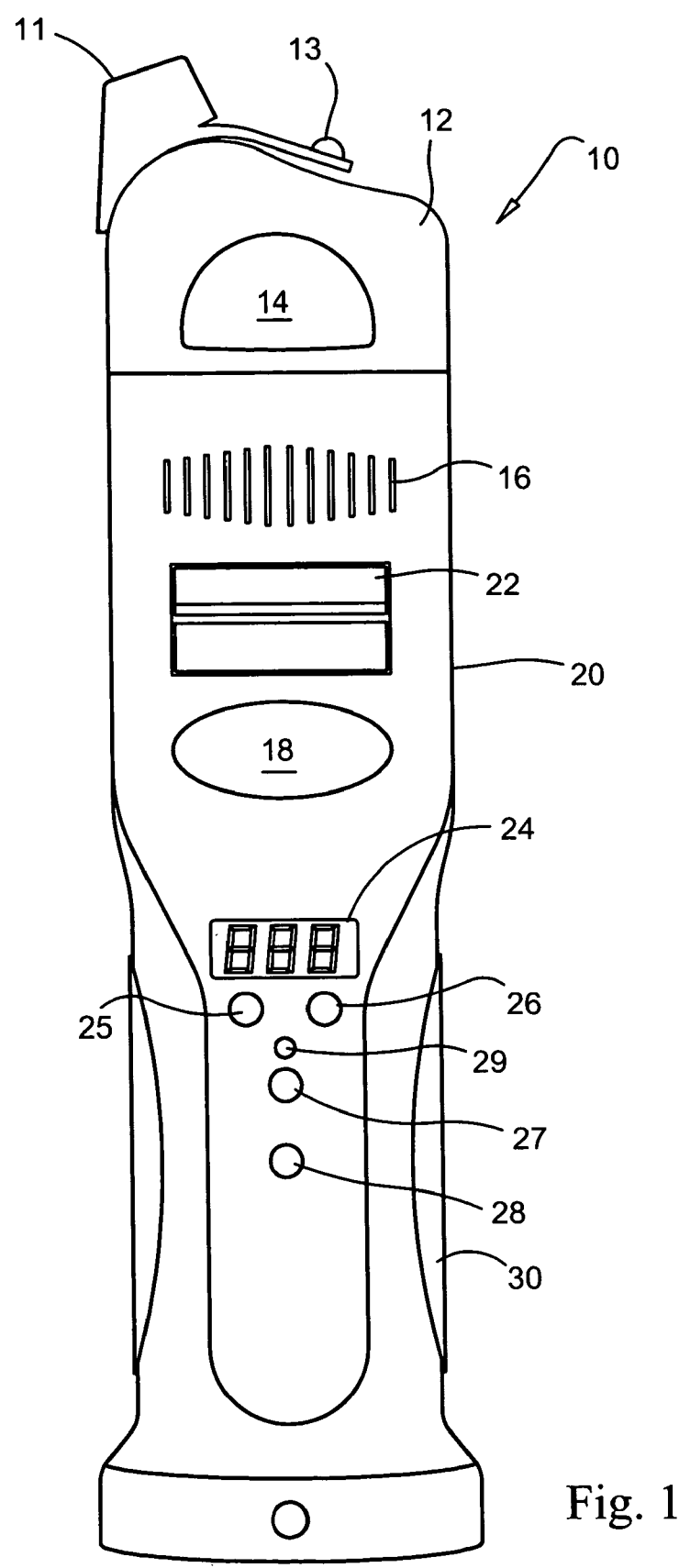
FIG. 1 is a front view of the present invention according to a preferred embodiment.
Figure 2:
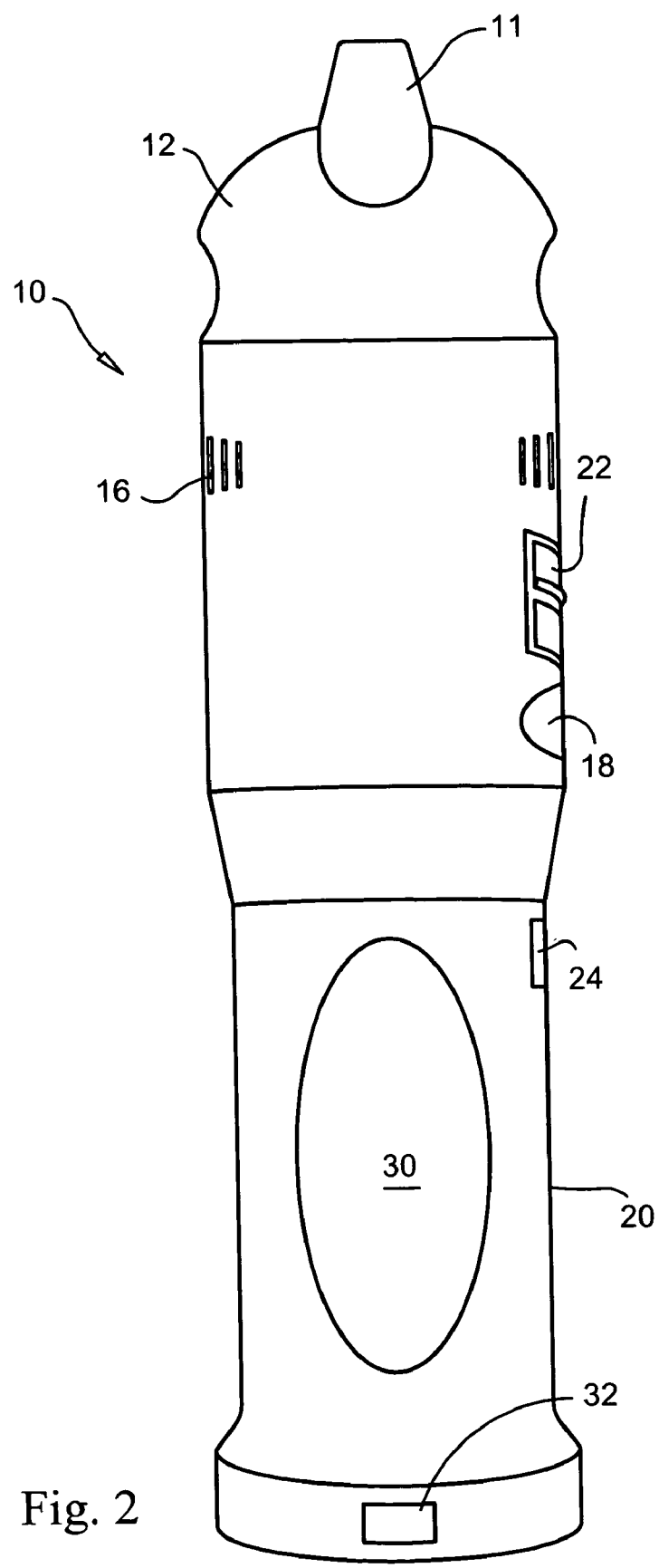
FIG. 2 is a side view of the present invention according to a preferred embodiment.

Referring to FIG. 1 and FIG. 2, shown is a preferred embodiment of the present invention, the apparatus 10 is made of a high heat and impact resistant nylon plastic fiber case 20. The apparatus 10 may have a switch means in communication with a power means for turning the apparatus on and off, such as switch 32. Switch 32 may have three positions (1) "charge mode" (2) "on mode" and (3) "adaptor mode". When switch 32 is in (1) charge mode or (3) adaptor mode power from an internal source may not be delivered. The power means may be an internal power source such as standard batteries or lithium ion batteries. Also, the apparatus 10 may utilize a power cord which allows for the power to be supplied by a standard electrical outlet. According to another embodiment, the apparatus 10 may have a rechargeable battery as the power means contained with and a charger stand, wherein the apparatus 10 may be placed and the apparatus 10 allowed to recharge. When switch 32 is the "on mode" position, the power means will deliver power.

The device may also have an information delivery and retrieval means in electrical, wireless, or optical communication with the power means. This may be a USB, firewire, ethernet, link interface, A/V interface, telephone cable interface, parallel interface, fiber optics, wireless ethernet and/or a serial interface connected to the apparatus and a separate information source (e.g. a personal computer, PDA, etc.). According to one embodiment, a USB cable may be connected to the apparatus 10 and a computer, wherein the computer delivers information to a time and temperature control means. This option may be used by doctors to regulate the dosage of a particular drug to a patient from a remote location or to download a patient's usage data from the device (e.g. how often it was used, at what settings, etc.) A doctor may also monitor and regulate their patients dosage and other aspects of treatment (e.g. airflow, temperature). Also, information may be stored externally, such as on a website for optimal temperatures and settings according to the substance being used. For example, a certain brand of tobacco may have an optimal vaporization program of 122 degrees for the first 2 minutes, the 100 degrees for the next 1 minute then 134 for the next 4 minutes then a constant 99 for 23 seconds. Instead of manually entering this data for every material the user can go to the website and download the software. Also, the user may know they are using a particular substance and there may be a code which would in turn direct the time and temperature control means. For instance, a code could be inputted into an information input/output means such buttons to effectuate an adjustment in the heating means and/or fan means such as to provide optimal vaporization.

The apparatus 10 works on convection, with the temperature controlled by a time and temperature control means which may be affected by a user pressing buttons. By way of example the time and temperature control means, according to a preferred embodiment, may be given a set of directions through the pressing of a left button 25 which may be used to reduce the temperature and the right button 26 may be used to increase the temperature. The temperature may be sensed by temperature sensing means (not shown), which is a small diode size sensor. These buttons may also be used to control the time the unit is on. The temperature may be viewed through the use of a display 24 which may be used to display the temperature and time. This may be a digital LCD or LED screen that displays the temperature and time elapsed. The LED light 29 may be used to indicate when the apparatus is on, charging or charged—it may turn a different color corresponding to each state. Buttons 27 and 28 may be used to program the device. By way of example "program set" button 27 may be used to set the temperature. For example, the temperature and time may be adjusted using left button 25 and right button 26, then the "program set" button 27 may be depressed in order to set the entered program. Left button 25, right button 26 and "program set" button 27 will deliver a set of instructions to the time and temperature control means, which will in turn deliver a set of directions to the heating means and fan means. Also, the "program set" button 27 may be used to turn on the heater. The "enter" button 28 is depressed after the "program set" button to activate the program. The air is directed by way of a fan means, and heated through the use of a heating means. The source material holder 22 may be inserted into the apparatus 10 and ejected from apparatus. Once the source material holder 22 is ejected, a substance may be placed in the source material holder which is contained within the source material holder 22 and heated air allowed to flow over the source material holder and the substance contained therein creating a vapor. The apparatus 10 may be programmed to be pre-heated, once an optimal temperature is reached the source material holder 22 may be ejected, a substance placed in the source material holder and the source material holder 22 and the source material holder 22 inserted back into the apparatus 10 and the materials vaporized.

According to another embodiment, the source material holder 22 would have a digitally encoded material holders that would recognize the substance contained therein and direct the time and temperature control means accordingly. By way of example, the disk may sense that the material contained with the disk in Marlboro™ brand tobacco. The optimal vaporization temperature for Marlboro brand tobacco is exactly 122° for the first two minutes, then 100° F. for the next one minute, then 134° F. for the next four minutes, then a constant 99° F. for 23 minutes. The optimal vaporization may also be provided by the information retrieval and delivery means and may be chosen from the group consisting of USB, firewire, ethernet, ilink interface, A/V interface, telephone cable interface, parallel interface, fiberoptic, wireless ethernet, and serial interface connected to the apparatus and an information source.

There may also be a mesh materials holder placed in the source material holder 22 to contain the substance, while allowing air to flow over the substance. Also, a tablet composed of compressed herbs or other substances molded into a shape which would allow receipt into the source material holder. It should be understood that the tablet may be composed of real drugs, biological drugs, pharmaceutical substances, synthetic or natural substances, hormones and/or insulin. The herbal tablet would have holes in it in order to allow the hot air to pass through it and vaporize the material. Also, oils, resins and other liquids may be used in the device by applying to a sponge material that may be placed in the source material holder or direct application to the substance. Tablets may also be made of a non-active material whose sole use is to be a carrier for liquid that is vaporized in the apparatus 10.

Window 18 may be used so that a user or a health care professional can monitor the vapor and make a visual ID of it. The air outlet vents 16 may be used to cool the heater. The air outlet vents 16 may also act as an exhaust for the fan means. The vaporized substance flows to the opening 11 in the top 12. The term top and second receptacle are intended to be equivalents and interchangeable. The top window 14 allows the user to see if vapor is occurring and allow the device to be used in complete darkness.

The vapor created by the apparatus is allowed to exit the device through an opening 11. It should be understood that the opening 11 may be used by an individual to inhale the vapor, but also the vapor may be allowed to flow out of the opening 11 and fill the surrounding area. When used by an individual to inhale the vapor through the opening it is desirable to be comfortably hand held. As such, there may be rubber grips 30 placed on the side of the apparatus for easy holding. The device may also be used as an aromatherapy device, wherein herbs are placed in the device and the vapor is allowed to fill the room.

FIG. 3 depicts the interior of the apparatus according to a preferred embodiment. As shown, the apparatus comprises in combination a power means 34 in electrical communication with a heating means 36 and a fan means 38, a thermocouple for sensing temperature, an information retrieval and delivery means in electrical communication with the power means 34, a time and temperature control means that adjusts the heat produced by the heating means 36 and length of time heat is produced, information output means in electrical communication with the power means 34 and a display 24 that displays the temperature and time; also a source material holder 22 which is insertable and removable for holding the substance, a venturi tube receptacle 40, a viewing means containing at least one light and an opening. The thermocouple for sensing temperature may be that depicted by temperature sensing means (not shown). It should be understood that the temperature sensing means (not shown) may be on the inside or outside of the venturi tube receptacle 40, the source material holder 22, or the heating means 36. The time and temperature control means produces a variable heat according to the specific substance being volatized in the apparatus. The heat provided by the heating means is preferably between 0° C. and 100° C. and the airflow between 0 and 10 Liters/min.

As used and according to a preferred embodiment, the housing is configured and sized to fit in the user's hand during use. The fan means 38 delivers air to create an air stream which combines with heat from the heating means 36 to provide a convection air stream, wherein the fan means 38 delivers air according to information provided by the information retrieval and delivery means and/or said time and temperature control means. An air stream is directed over a source material holder 22 which includes a cavity for holding a substance, creating a substance vapor air stream and venturi tube receptacle 40 having at least one opening in communication with the source material holder receives the substance vapor air stream. The heater is preferably a Ceramic UF Heater. The apparatus may also release the volatile elements from the opening into the ambient air. Time and temperature control means produces a variable heat according to the specific substance being volatized in the apparatus. Also, as discussed in previous embodiments, the information input/output means may be in electrical communication with the time and temperature control means, and power means and allow for adjustment of the temperature, time and airflow. Information may also be manually entered into said information input/output means which in turn electrically communicates with said power means, heating means and fan means to adjust the temperature within said apparatus for a specified time. The information retrieval and delivery means may also be a disk contained within said apparatus which automatically senses the nature of the material and provides information to the apparatus such as to provide optimal release of volatile elements of the substance. A mesh materials holder contained within the source material holder 22 may be used in order to prevent the inhalation of extraneous particles and to contain the substance. The mesh materials holder may also have a substance embedded in it. According to another embodiment, a pre-formed substance with holes formed to be contained within the source material holder.

FIG. 4 depicts a top view of the present invention according to a preferred embodiment. As shown, the top 12 has an opening 11. There may also be a chin rest 13. This may be useful for the user to rest their chin on while inhaling the vapor released through said opening 11.

FIG. 5 depicts a method of releasing volatile elements of a substance. The method comprising the steps of: Step 198 heating a substance using a heating means 36. Step 199 may be inputting information manually into an information input/output means, and adjusting the temperature within said apparatus for a specified period of time according to information obtained from the information input/output means. Adjustments in the power means 34, heating means 36 and the fan means 38 may control the temperature within the apparatus for a specified time. Step 200 may be providing a variable heat by the time and temperature control means according to the specific substance being volatized in the apparatus 10. Step 202 delivering air using a fan means 38 to create an air stream. Step 204 combining heat from the heating means 36 and the air stream to provide a convection air stream. Step 206 may be delivering the convection air stream according to information provided by the information retrieval and delivery means. Step 208 may be delivering the convection air stream according to information provided by the temperature control means. Step 210 directing the convection air stream over a source material holder 22, wherein the source material holder 22 may include a cavity for holding a substance. Step 212 creating a substance vapor air stream. Step 214 may be releasing volatile elements from the opening 11 into the ambient air. Step 216 may be receiving the substance vapor air stream by the venture tube receptacle 40, wherein the venture tube receptacle 40 may have at least one opening in communication with the source material holder 22.

It should be understood that the foregoing relates to preferred embodiments of the invention and that modifications may be made without departing from the spirit and scope of the invention as set forth in the following claims.

We claim:

1. An apparatus that allows for the inhalation of the active elements of a substance comprising; a housing configured and sized to fit in the user's band during use; a power means that supplies power to a heating means, information retrieval and delivery means, time and temperature control means where said time and temperature control means produces a variable heat according to the specific substance being volatized in said apparatus, information input/output means where said information input/output means is in electrical, digital, optical or wireless communication with said power means and allows for adjustment of temperature and air flow, display means, fan means and cooling means; wherein said fan means delivers air to create an air steam which combines with heat from said heating means to provide a convection air stream; wherein said fan means delivers air according to information provided by said information retrieval and delivery means or said time and temperature control means; said convection air stream is directed over a source material holder which includes a cavity for holding a substance, creating a substance vapor air stream; said housing having therein a receptacle having at least one opening in communication with said source material holder for receiving said substance vapor air stream; wherein said apparatus allows the release of volatile element from said opening into the ambient air; wherein said time and temperature control means produces a variable heat according to the specific substance being volatized in said apparatus; where information is manually entered into said information input/output means which in turn electrically communicates with said power means, heating means and fan means to adjust the temperature within said apparatus for a specified time; where said information retrieval and delivery means is chosen from the group consisting of USB, firewire, ethernet, ilink interface, fiber optic, wireless Ethernet A/V interface, telephone cable interface, parallel interface, and serial interface connected to said apparatus and an information source.

2. An apparatus as in claim 1, wherein said heating means is a Ceramic UF Heater.

3. An apparatus as in claim 1, wherein said receptacle for receiving said vapor is a Venturi tube receptacle.

4. An apparatus as in claim 1, wherein said airstream has a flow between 0 and 10 Liters/min.

5. A method of releasing volatile elements of a substance comprising the steps of: heating a substance using a heating means; delivering air using a fan means to create an air stream; combining heat from the heating means and said air stream to provide a convection air stream; directing said convection air stream over a source material holder; creating a substance vapor air stream; delivering said convection air stream according to information provided by the information retrieval and delivery means according to information provided by the temperature control means; receiving by said venturi tube receptacle said substance vapor air stream where said venturi tube receptacle has at least one opening in communication with the source material holder; producing a variable heat by said time and temperature control means according to the specific substance being volatized in the apparatus.

6. A method as in claim 5 further comprising the steps of: inputting information manually into an information input/output means; adjusting the temperature within said apparatus for a specified period of time according to information obtained from said information input/output means.

7. A method as in claim 6, wherein said step of adjusting the temperature is performed via adjustments in said power means, said healing means and said fan means.

* * * * *